US012741969B2

(12) United States Patent
Zhang et al.

(10) Patent No.: US 12,741,969 B2
(45) Date of Patent: Sep. 22, 2026

(54) PROCESS FOR THE PREPARATION OF 2-BROMO-4-(3,5-DIFLUOROPHENYL)-4,5,6,7-TETRAHYDRO-[1,2,4]TRIAZOLO[1,5-A] PYRIMIDINE

(71) Applicant: Hoffmann-La Roche Inc., Little Falls, NJ (US)

(72) Inventors: Guocai Zhang, Shanghai (CN); Weichun Chen, Shanghai (CN)

(73) Assignee: Hoffmann-La Roche Inc., Branchburg, NJ (US)

( * ) Notice: Subject to any disclaimer, the term of this patent is extended or adjusted under 35 U.S.C. 154(b) by 518 days.

(21) Appl. No.: 18/256,629

(22) PCT Filed: Dec. 8, 2021

(86) PCT No.: PCT/EP2021/084734
§ 371 (c)(1),
(2) Date: Jun. 8, 2023

(87) PCT Pub. No.: WO2022/122800
PCT Pub. Date: Jun. 16, 2022

(65) Prior Publication Data

US 2024/0025911 A1 Jan. 25, 2024

(30) Foreign Application Priority Data

Dec. 10, 2020 (WO) ................ PCT/CN2020/135294

(51) Int. Cl.
*C07D 487/04* (2006.01)
*B01J 31/04* (2006.01)

(52) U.S. Cl.
CPC ............ *C07D 487/04* (2013.01); *B01J 31/04* (2013.01)

(58) Field of Classification Search
CPC .................................................... C07D 487/04
USPC .......................................................... 544/263
See application file for complete search history.

(56) References Cited

FOREIGN PATENT DOCUMENTS

| | | | |
|---|---|---|---|
| WO | 2011/092272 | A1 | 8/2011 |
| WO | 2018/060300 | A1 | 4/2018 |
| WO | 2018/065340 | A1 | 4/2018 |
| WO | 2018/087018 | A1 | 5/2018 |
| WO | 2019/141832 | A1 | 7/2019 |

OTHER PUBLICATIONS

International Preliminary Report on Patentability—PCT/EP2021/084734 issued Jun. 13, 2023, pp. 1-8.
International Search Report with Written Opinion—PCT/EP2021/084734 mailed Apr. 13, 2022, pp. 1-14.
Ratni, H., et al., "Discovery of RO7185876, a Highly Potent γ-Secretase Modulator (GSM) as a Potential Treatment for Alzheimer's Disease" ACS Med Chem Lett 11(6):1257-1268 (Jun. 11, 2020).
Ratni, H., et al., "Supporting Informations—Discovery of RO7185876, a Highly Potent γ-Secretase Modulator (GSM) as a Potential Treatment for Alzheimer's Disease" ACS Med Chem Lett (Supporting Information), 11(6):1-13 (Jun. 11, 2020).

*Primary Examiner* — Douglas M Willis
(74) *Attorney, Agent, or Firm* — Genentech, Inc.

(57) ABSTRACT

The present disclosure provides a process for preparing 2-bromo-4-(3,5-difluorophenyl)-4,5,6,7-tetrahydro-5H-[1,2,4]triazolo[1,5-a]pyrimidine. In one example, a corresponding precursor compound is reacted with triphenylphosphine and an azodicarboxylate reagent in an organic solvent at a reduced temperature to form the desired triazolopyrimidine compound. The reaction mixture is quenched with water and extracted with an organic solvent. The combined organic layers are washed with an aqueous salt solution, dried, and concentrated. The resulting residue is treated with an alcohol solvent, and the solid is isolated by filtration. The isolated material is further treated with an ester solvent at an elevated temperature, cooled, isolated by filtration, and dried to provide 2-bromo-4-(3,5-difluorophenyl)-4,5,6,7-tetrahydro-5H-[1,2,4]triazolo[1,5-a]pyrimidine.

15 Claims, No Drawings

PROCESS FOR THE PREPARATION OF 2-BROMO-4-(3,5-DIFLUOROPHENYL)-4,5,6,7-TETRAHYDRO-[1,2,4]TRIAZOLO[1,5-A]PYRIMIDINE

CROSS-REFERENCE TO RELATED APPLICATIONS

This application is the National Stage Entry under 35 U.S.C. § 371 of International Application No. PCT/EP2021/084734, filed Dec. 8, 2021, which claims benefit of priority under 35 U.S.C. § 119 (a) to Application No. PCT/CN2020/135294 filed on Dec. 10, 2020, each of which is incorporated herein by reference in their entirety.

The present invention relates to a process for the preparation of a compound (I), (I)

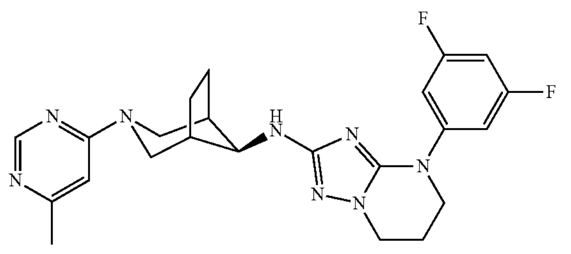

or pharmaceutically acceptable salt thereof, which is a modulator of γ-secretase and may be useful for prophylaxis and treatment of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

BACKGROUND OF THE INVENTION

The synthetic approach of compound (I) was disclosed in WO2018060300, and WO2018065340. However, the current processes are not suitable for large-scale production due to the following issues:

(a) seven linear synthesis steps with very low yield, e.g., 19.8% for producing

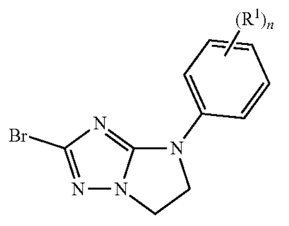

and 62% for making

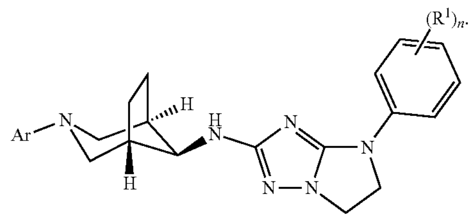

(b) column purification with tedious work up process for all of the intermediates, such as: intermediates

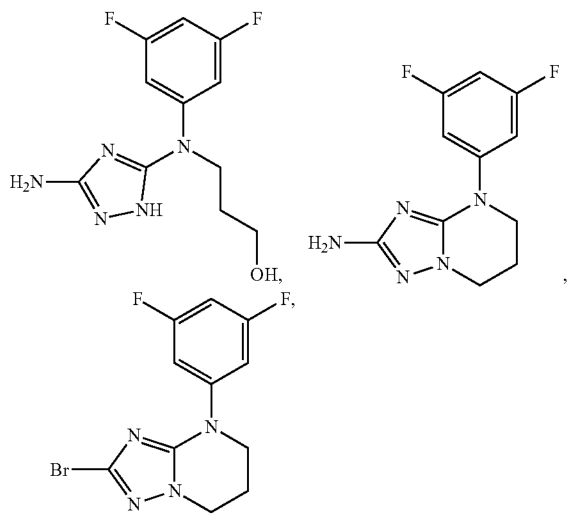

and the final product.

(c) safety concern with toxic reagent of hydrazine.

(d) use of high loading of expensive catalyst Pd (20%) which could result higher cost for large scale API production and complicated process to remove the catalyst.

(e) high cost with HPLC separation.

(f) safety, repeatability, and scalability concerns for the newly form tri-azole ring during large-scale production.

SUMMARY OF THE INVENTION

Based on the issues above, one object of this invention therefore is to find an efficient synthetic approach, which can address some or all of above issues and be applied on a technical scale.

One aspect of the present invention relates to a process for the preparation of compound (I), (I)

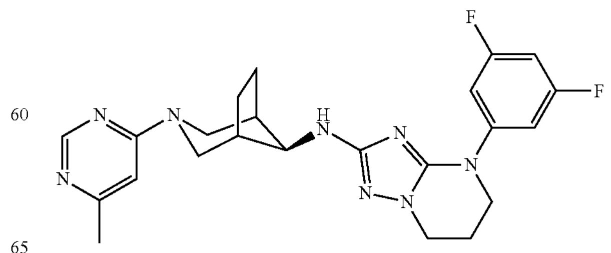

or pharmaceutically acceptable salt thereof.

Another aspect of the present invention relates to novel processes for the preparation of compound (III) and compound (IV):

(IX)

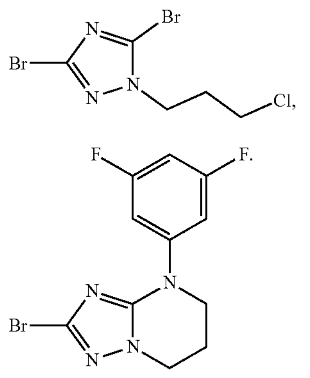

(IV)

The advantages of the process of the present invention include, but not limited to, one or more of the following:

(a) Totally new process with less steps;

(b) Safe and robust for scale up, no tri-azole ring formation step;

(c) Practice work up process, no column purification.

In another embodiment, provided herein is a pharmaceutical composition comprising compound (I); and a pharmaceutically acceptable carrier, excipient, diluent, adjuvant, vehicle or a combination thereof.

In another embodiment, provided herein is compound (I) for the treatment or prophylaxis of a disease associated with the deposition of β-amyloid in the brain, in particular Alzheimer's disease, or a disease selected from cerebral amyloid angiopathy, hereditary cerebral hemorrhage with amyloidosis, Dutch-type (HCHWA-D), multi-infarct dementia, dementia pugilistica and Down syndrome.

In another embodiment, provided herein is the use of compound (I) for the treatment or prophylaxis of a disease associated with the deposition of β-amyloid in the brain, in particular Alzheimer's disease, or a disease selected from cerebral amyloid angiopathy, hereditary cerebral hemorrhage with amyloidosis, Dutch-type (HCHWA-D), multi-infarct dementia, dementia pugilistica and Down syndrome.

In another embodiment, provided herein is the use of compound (I) or the pharmaceutical composition for the manufacture of a medicament for the treatment or prophylaxis of a disease associated with the deposition of β-amyloid in the brain, in particular Alzheimer's disease, or a disease selected from cerebral amyloid angiopathy, hereditary cerebral hemorrhage with amyloidosis, Dutch-type (HCHWA-D), multi-infarct dementia, dementia pugilistica and Down syndrome.

In another embodiment, provided herein is a method for the treatment or prophylaxis of a disease associated with the deposition of β-amyloid in the brain, in particular Alzheimer's disease, or a disease selected from cerebral amyloid angiopathy, hereditary cerebral hemorrhage with amyloidosis, Dutch-type (HCHWA-D), multi-infarct dementia, dementia pugilistica and Down syndrome, which method comprises administering a therapeutically effective amount of compound (I) or the pharmaceutical composition disclosed herein.

DETAILED DESCRIPTION OF THE INVENTION

Definitions

The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457.

ABBREVIATION

API Active Pharmaceutical Ingredient
$(Boc)_2O$ Di-tert-butyl dicarbonate
DCM Dichloromethane
DEAD Diethyl azodicarboxylate
DIPEA N,N-Diisopropylethylamine
DMF Dimethylformamide
DMSO Dimethyl sulfoxide
Eq Equivalent
EtOAc or EA Ethyl acetate
EtOH Ethanol
IPA Isopropanol
IP Ac Isopropyl acetate
$K_2CO_3$ Potassium carbonate
KOAc Potassium acetate
KOH Potassium Hydroxide
$Pd_2(dba)_3$ Tris(dibenzylideneacetone)dipalladium(0)
$Pd(OAc)_2$ Palladium (II) acetate
LiHMDS Lithium bis(trimethylsilyl)amide
2-MeTHF 2-Methyltetrahydrofuran
MeOH Methanol
MOM Methoxymethyl
$MgSO_4$ Magnesium sulfate
MTBE Methyl tert-butyl ether
NaH Sodium hybrid
NaHMDS Sodium bis(trimethylsilyl)amide
NaOAc Sodium acetate
NaOtBu Sodium tert-butanol
$NH_4Cl$ Ammonium Chloride
NMP N-Methyl-2-pyrrolidone
$PPh_3$ Triphenyl phosphine
SEM 2-(Trimethylsilyl) ethoxymethyl
tBuOH tert-Butanol
TEA Triethylamine
THF Tetrahydrofuran
TFA Trifluoroacetic acid
v/V Volume ratio wt. % Weight percentage
The present invention provides innovative processes as outlined in the schemes 1 to 3.
Scheme 1
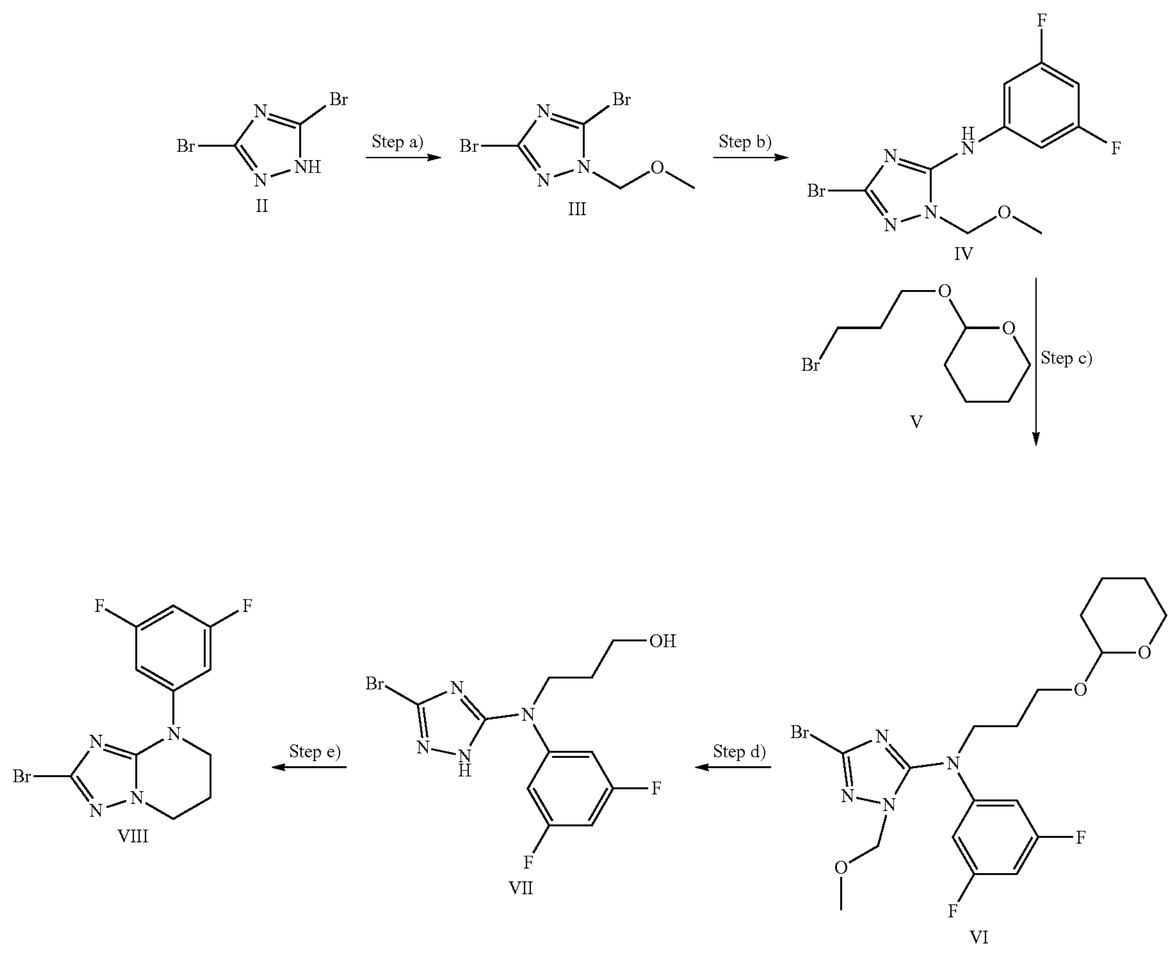
The synthesis comprises the following steps:
step a) the formation of compound (III),
(III)
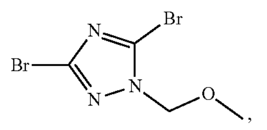
via the reaction of compound (II)
(II)
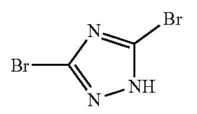
and MOMChloride;
step b) the formation of compound (IV),
(IV)
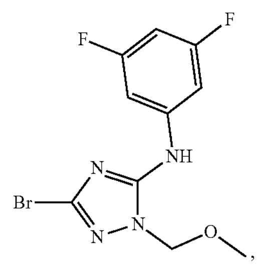

via alkylation reaction of compound (III) and 3,5-difluoroaniline;

step c) the formation of compound (VI), (VI)

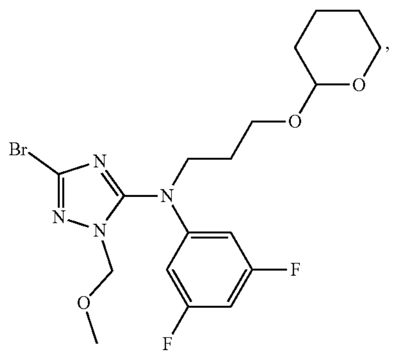

via the reaction of compound (IV) and compound (V)

(V)

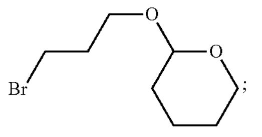

step d) the formation of compound (VII), (VII)

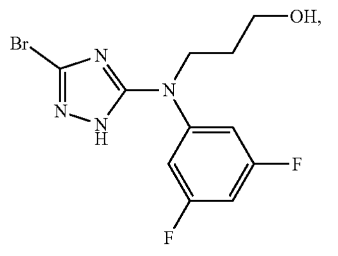

via the de-protection reaction of compound (VI);

Step e) the formation of compound (VIII), (VIII)

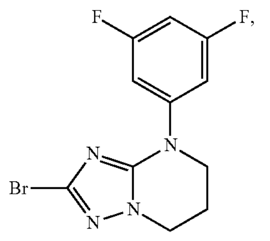

via the internal Mitsunobu cyclization reaction of compound (VII).

A detailed description of Steps a) to e) is as follows:

Step a) the formation of compound (III), (III)

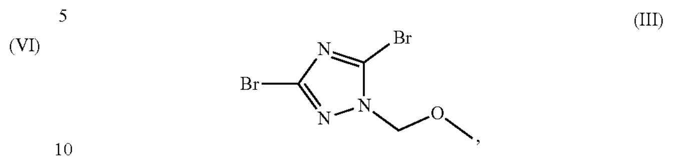

via the reaction of compound (II), (II)

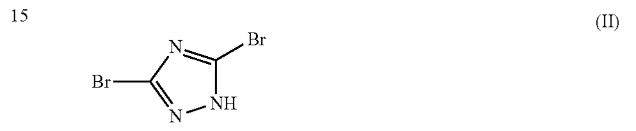

and MOMChloride.

Compound (III) is synthesized in the presence of a suitable solvent, and a suitable base.

The suitable solvent is selected from DCM and THF; preferably, the solvent is THF.

The suitable base is selected from KOAc, NaOAc and NaH; preferably, the suitable base is NaH.

Step b) the formation of compound (IV), (IV)

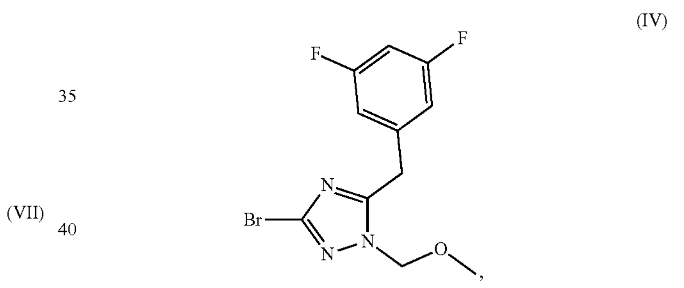

via alkylation reaction from compound (III) and 3,5-difluoroaniline;

Compound (IV) is synthesized in a suitable solvent with a suitable base.

The suitable solvent is selected from 2-MeTHF, DCM and THF; preferably, the solvent is THF.

The suitable base is selected from NaHMDS, $K_2CO_3$, KOH, NaOH, NaH and LiHMDS; preferably, the base is LiHMDS.

The suitable equivalent of the suitable base is from 1.0 eq. to 2.5 eq.; preferably, the equivalent is selected from about 1.0 eq., about 1.2 eq., about 1.5 eq., about 2.0 eq. and about 2.5 eq.; more preferably, the equivalent is about 2.0 eq.

The suitable equivalent of 3,5-difluoroaniline is from 1.0 eq. to 2.5 eq.; preferably, the equivalent is selected from about 1.0 eq., about 1.2 eq., about 1.5 eq., about 2.0 eq. and about 2.5 eq.; more preferably, the equivalent is about 2.5 eq.

The reaction is performed at −20~70° C., 10~70° C., preferably at 25~30° C.

The temperature system designed in present invention gives high yield and good purge effect for impurities.

Step c) the formation of compound (VI), (VI)

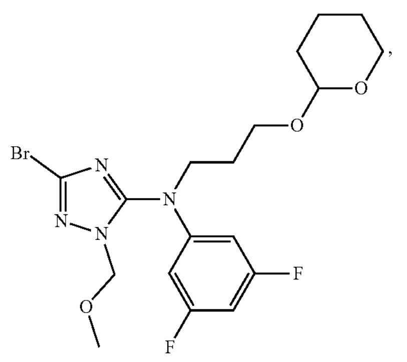

via the reaction of compound (IV) and compound (V)

(V)

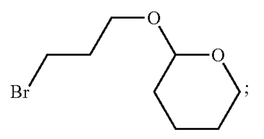

Compound (VI) is synthesized in the presence of the compound (V) with a suitable amount of base.

The suitable amount of compound (V) is 1.7 eq.~2.26 eq.; preferably, the equivalent is about 1.7 equivalent.

The suitable base is selected from NaOH, $Na_2CO_3$, $Cs_2CO_3$ and potassium carbonate; preferably, the base is potassium carbonate.

The suitable amount of base is 2.0 eq.~3.0 eq.; preferably, the amount is about 2.06 equivalent.

Step d) the formation of compound (VII), (VII)

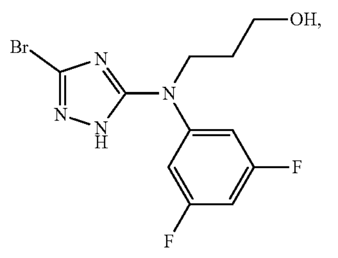

via the de-protection reaction of compound (VI);

Compound (VII) in this step is synthesized via de-protection reaction in the presence of a suitable volume of acid.

The suitable acid is selected from HBr, TFA and HCl; preferably, the acid is HCl; more preferably, the acid is HCl (36.5% wt.) in water.

The suitable volume of acid used in de-protection reaction is 1 V to 2 V; preferably, the volume is about 2 V.

Step e) the formation of compound (VIII), (VIII)

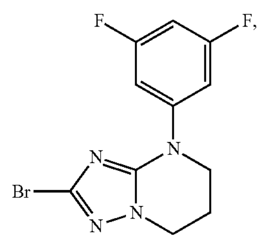

via the internal Mitsunobu cyclization reaction of compound (VII).

Compound (VIII) is cyclization in the presence of DEAD, $PPh_3$ with a suitable volume of solvent.

The suitable solvent is selected from DMSO, NMP, and DMF; preferably, the solvent is DMF.

The suitable volume of solvent is from 5 V to 10 V; preferably the volume is about 5 V.

Scheme 2

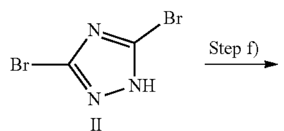

II

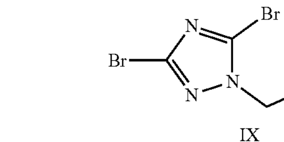

IX

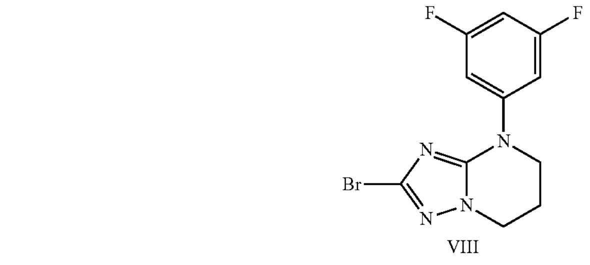

VIII

The synthesis comprises the following steps:

step f) the formation of compound (IX), (IX)

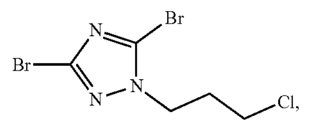

via the reaction of compound (II), (II)

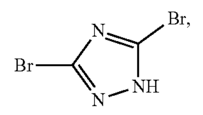

and 1-chloro-3-iodo-propane.

step g) the formation of compound (VIII), (VIII)

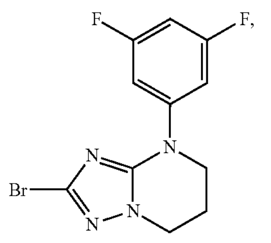

via telescope alkylation reaction from compound (IX) and 3,5-difluoroaniline.

A detailed description of Steps f)-g) is as follows:

Step f) the formation of compound (IX), (IX)

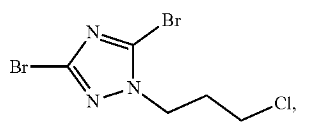

via the reaction of compound (II), (II)

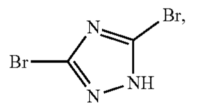

and 1-chloro-3-iodo-propane

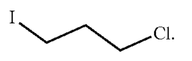

Compound of formula (IX) is synthesized in the presence of a suitable solvent with a suitable base.

The suitable solvent is selected from MeTHF and THF; preferably, the solvent is THF.

The suitable base is selected from KOAc, NaOAc, NaOH, KOH, $K_2CO_3$ and $Na_2CO_3$; preferably, the suitable base is $K_2CO_3$.

The reaction is performed at 0° C.~70° C., preferably at 20° C.~30° C., more preferably at 20° C.~25° C.

Dimer

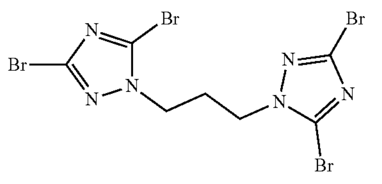 [SMILES: Brc1nc(Br)n(CCCn2nc(Br)nc2Br)n1]

was detected while diboromopropane or dichloropropane was employed as alkylation reagent, which are unsuitable for large scale manufacture due to poor selectivity. In present invention, 1-chloro-3-iodo-propane was employed to provide compound (IX), which can be controlled well to avoid the dimer impurity in large-scale manufacture.

Step g) the formation of compound (VIII), (VIII)

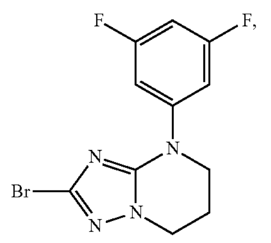

via telescope alkylation reaction from compound (IX) and 3,5-difluoroaniline.

Compound (VIII) is synthesized in a suitable solvent with a suitable base.

The suitable solvent is selected from 2-MeTHF, DCM and THF; preferably, the solvent is 2-MeTHF.

The suitable base is selected from NaHMDS, $K_2CO_3$, KOH, NaOH, NaH and LiHMDS; preferably, the base is LiHMDS.

The suitable equivalent of base is from 1.0 eq to 3.75 eq; preferably, the equivalent is 1.0 eq, 1.2 eq, 1.5 eq or 3.75 eq; more preferably, the equivalent is 3.75 eq.

The suitable equivalent of 3,5-difluoroaniline is from 1.0 eq to 1.5 eq, preferably, the equivalent is selected from 1.0 eq, 1.2 eq and 1.5 eq; preferably, the equivalent is 1.2 eq.

The reaction is performed at −20° C.~70° C., preferably at 0° C.~25° C., more preferably first at 0° C.~5° C., then at 20° C.~25° C.

Temperature is critical for the whole process in terms of cyclization. In present invention, step g) can be run for 2 stages, which are telescoped without solid isolation. The temperature for step g) of present invention gives high yield and good purge effect for impurities.

Scheme 3

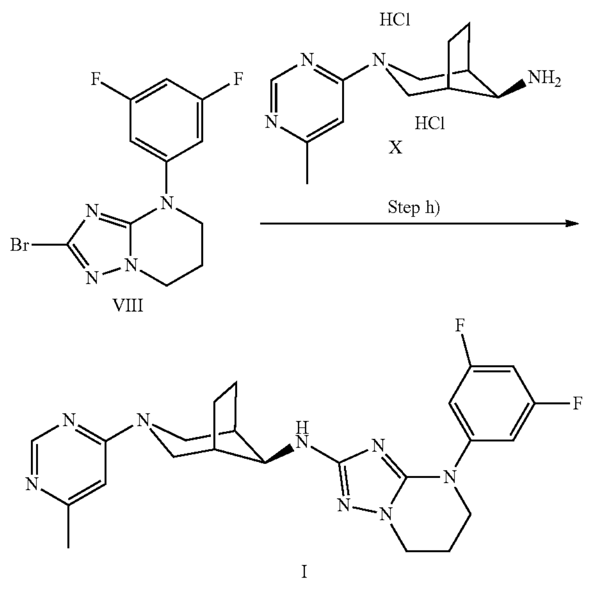

X

VIII

I

Step h) the formation of compound (I), (I)

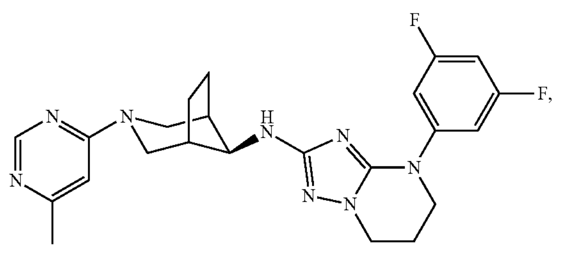

via Buchwald cross coupling reaction of compound (VIII) and compound (X) (prepared according to the process described in WO 2019141832).

A detailed description of Step h) is as following:

Compound (I) in this step is synthesized via Buchwald cross coupling reaction in the presence of a suitable catalyst, base and ligand in a suitable solvent. The compound (I) is purified through recrystallization which was performed in a suitable solvent.

The suitable catalyst used in cross coupling reaction is selected from $Pd_2(dba_3)\cdot CHCl_3$, $Pd(OAc)_2$; preferably, the catalyst is $Pd_2(dba_3)\cdot CHCl_3$.

The suitable base used in cross coupling reaction is selected from $Na_2CO_3$, $K_2CO_3$, $NaHCO_3$, $KHCO_3$, NaOH, KOH and NaOtBu; preferably, the base is NaOtBu.

The suitable solvent used in cross coupling reaction is selected from IPAc, EtOAc, MTBE, toluene, THF and 2-MeTHF; preferably, the solvent is 2-MeTHF.

The cross coupling reaction is performed in a suitable solvent at 20° C.~80° C., preferably at 70° C.~75° C.

The ligand is selected from BrettPhos, AdCyBrettPhos, tBuBrettPhos, AdBrettPhos, RocPhos, tBuXphos, BippyPhos, MeatBuXphos and Me3MeOtBuXphos, preferably, the ligand is tBuXphos.

The recrystallization is performed in a suitable solvent at 20° C.~80° C., preferably at 70° C.~75° C.; wherein the suitable solvent is selected from heptane, hexane and petroleum ether; preferably, the solvent is heptane; more preferably, the solvent is n-heptane.

For recrystallization, the pH of the solution was adjusted to 3~8; preferably, the pH of the solution was first adjusted to 3~4 to get a clear solution and then to 7~8.

The recrystallization condition in this invention can produce high yield product with good purge effect for impurities and excess residual solvent.

EXAMPLES

The invention will be better understood by reference to the following examples. They should not, however, be construed as limiting the scope of the invention.

Example 1

3,5-dibromo-1H-1,2,4-triazole (Compound (III))

(III)

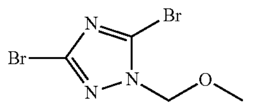

To a THF (3.5 L) solution of NaH (125 g, 3.11 mol, 1.1 eq.) in a 10 L glass-lined reactor was charged with 3, 5-dibromo-1H-1, 2,4-triazole (641 g, 2.83 mol) in portions slowly at 0~5° C. After being stirred for 1 hours at 0~5° C., the MOMchloride (275 g, 3.40 mol) was added dropwise to the mixture at 0° C. The mixture was stirred at 20~25° C. for 16 hours. Ice water (6.5 kg, 10 v) was added dropwise to quench the reaction mixture at 0~5° C. and then extracted with EA (6.5 L) 3 times. The combined organic layer was washed with water (6.5 kg) and 20% wt NaCl aqueous solution (6.5 kg), then concentrated to afford compound (III) (613 kg, 80% yield, 99.4% purity).

Compound (III): 1H NMR (400 MHz, $CDCl_3$) δ=5.44 (s, 2H), 3.47 (s, 3H).

$[M+H]^+$=269.8

Example 2

5-bromo-N-(3,5-difluorophenyl)-2-(methoxymethyl)-1,2,4-triazol-3-amine (Compound (IV))

(IV)

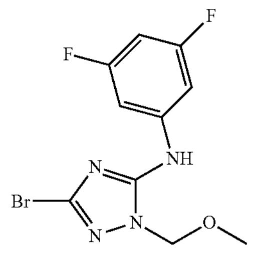

To an anhydrous THF (3 L) solution of compound (III) (613 g, 2.3 mol) in 10 L glass-lined reactor was charged with 3,5-difluoroaniline (741 g, 5.75 mol, 2.5 eq.) at 20~25° C. After being stirred for 30 min and cooled to 0~5° C., LiHMDS (1M in THF, 4.6 L, 4.6 mol, 2.0 eq.) was added dropwise at 0~5° C. The reaction mixture was allowed warm to 25~30° C. with stirring for another 16 hours. Saturated aqueous $NH_4Cl$ solution (6.1 kg, 10 v) was added dropwise to the reaction mixture to quench the reaction at 0~5° C. and then extracted with EA (6.5 L) 3 times. The combined organic layer was washed with water (6.5 kg) and 20% wt NaCl aqueous solution (6.5 kg), then concentrated under vacuum. Petroleum (3.2 kg) was added to the reaction mixture, and then slurred for 1 h at 20~25° C. The solid was separated via filtration and was washed with petroleum (1 kg). The filtrate was dried in vacuum oven (30 mmHg, 40° C.) for 32 hours to afford compound (IV) (541 g, 75% yield, 98.8% purity).

Compound (IV): 1H NMR (400 MHz, DMSO-$d_6$) δ=7.14-7.11 (t, 1H), 6.94 (s, 1H), 5.40 (s, 2H), 3.46 (s, 1H).

$[M+H]^+$=320.8

A series of studies were carried out to demonstrate the impact of reaction temperature, which showed that 25~30° C. is the best condition for the alkylation reaction. In addition, 2.0 equivalent of LiHMDS and 2.5 equivalent of 3,5-difluoroaniline provide better result.

| Test No. | LiHMDS | 3,5-Difluoroaniline | temperature | Remaining Compound (III) |
|---|---|---|---|---|
| 1 | 2.0 eq. | 2.5 eq. | 25° C.~30° C. | 0.9% |
| 2 | 1.5 eq. | 1.5 eq. | 5° C.~10° C. | 13.6% |
| 3 | 2.0 eq. | 2.0 eq. | 5° C.~10° C. | 7.1% |
| 4 | 2.0 eq. | 2.0 eq. | 25° C.~30° C. | 5.2% |

Example 3

5-bromo-N-(3,5-difluorophenyl)-2-(methoxymethyl)-N-(3-tetrahydropyran-2-yloxypropyl)-1, 2, 4-triazol-3-amine (Compound (VI))

(VI)

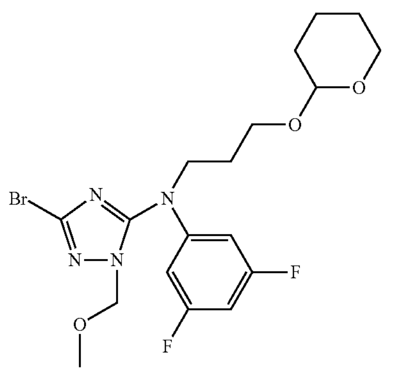

To a DMF (4000 mL) solution of compound (IV) (843 g, 2.64 mol) in 10 L glass-lined reactor was charged with $K_2CO_3$ (750 g, 5.43 mol, 2.06 eq.) and 2-(3-Bromopropoxy) tetrahydropyran (1000 g, 4.48 mol, 1.7 eq.) at 20~25° C. and stirred for 16 hours. The resulting reaction mixture was cooled to 0~5° C. Water (3 kg) was added to the reaction mixture and then extracted with EA (6.5 L) 3 times. The combined organic layers were washed with water (6.5 kg) and 20% wt NaCl aqueous solution (6.5 kg), then concentrated to afford compound (VI) (1.51 kg, 100% yield, 94.0% purity) as brown oil, the oil was be used in the next step without further purification.

Compound (VI): 1H NMR (400 MHz, DMSO-$d_6$) δ=6.54-6.47 (dd, 2H), 5.02 (s, 1H), 4.60-4.58 (d, 2H), 3.97-3.81 (m, 5H), 3.64-3.45 (m, 3H), 3.36 (s, 3H), 1.99-1.56 (m, 13H).

Example 4

3-(N-(3-bromo-1H-1, 2, 4-triazol-5-yl)-3, 5-difluoro-anilino) propan-1-ocarbamate (Compound (VII))

(VII)

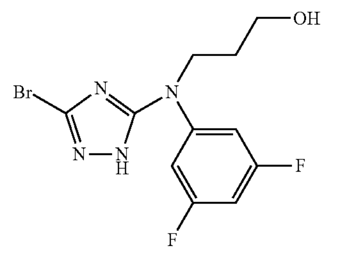

To a 20 L glass-lined reactor was charged with compound (VI) (1510 g), methanol (6000 mL), hydrochloride acid (2.4 L) and water (2.4 L) at 20~25° C., then the mixture was heated to 70~75° C. and stirred for 5 hours. The resulting reaction mixture was cooled to at 20~25° C., concentrate to remove the methanol, and then adjusted the residue to pH=8~9 with 4N aq. NaOH (6.9 L). The resulting reaction mixture was extracted with EA (15 L) twice. The combined organic layers was washed with brine with 20% wt NaCl aqueous solution (20 L), dried through $Mg_2SO_4$, concentrated to remove the solvent. To the resulting reaction mixture was added EA (2 L), then heated to 50~55° C., then heptane (6 L) was added dropwise to the reaction mixture, and then cooled to 20~25° C. during 6 h and stirred for another 1 h. The solid was separated via filter and washed with EA/Heptane (1/3, 500 mL), and dried in vacuum (30 mmHg, 40° C.) for 16 hours to afford compound (VII) (621 g, 70% yield, 99.0% purity) as white solid.

Compound (VII): 1H NMR: (400 MHz, $CDCl_3$) δ ppm: 12.17-10.22 (s, 1H), 6.90-6.88 (dd, 2H), 6.66-6.60 (t, 1H), 4.03-3.99 (t, 2H), 3.71-3.68 (d, 2H), 1.88-1.85 (t, 2H).

Example 5

2-bromo-4-(3,5-difluorophenyl)-6,7-dihydro-5H-[1, 2,4]triazolo[1,5-a]pyrimidine (Compound (I))

(VIII)

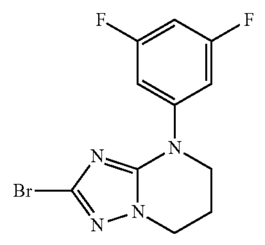

To a 10 L glass line reactor was charged with compound (VII) (621 g, 1.86 mol), DMF (4 L), $PPh_3$ (800 g, 3.05 mol, 1.64 eq.) at 20~25° C. The resulting mixture was cooled to −20~10° C., then DEAD (500 g, 2.87 mol) was added dropwise into mixture at −20~−10° C. and stirred for 3 hours. Water (6.21 kg, 10 v) was added dropwise to the reaction mixture to quench the reaction at 0~5° C. and then extracted with EA (6.5 L) 3 times. The combined organic layers was washed with 20% wt NaCl aqueous solution (10 L), dried through $Mg_2SO_4$, concentrated to remove the solvent. The resulting residual was diluted with MeOH (6.2 L, 10 V) at 20~25° C. and stirred for 1 hours, then the solid was separated via filter and rinsed with MeOH (600 mL).

The resulting residual was diluted with EA (6.2 L, 10 V) at 20~25° C., then heated to 70~75° C. and stirred for 1 hours. The resulting mixture was cooled to 20~25° C., then the solid was separated via filter and rinsed with EA (600 mL). The resulting cake was dried in vacuum oven (30 mmHg, 40° C.) for 16 hours to afford compound (I) (287 g, 48.0% yield, 98.0% purity) as white solid.

Compound (VIII): 1H NMR (400 MHz, DMSO-$d_6$) δ=7.39-7.34 (m, 2H), 6.97-6.92 (m, 1H), 4.11-4.08 (m, 2H), 3.85-3.83 (m, 2H), 2.26-2.20 (m, 2H).

Example 6

3,5-dibromo-1H-1,2,4-triazole (compound IX)

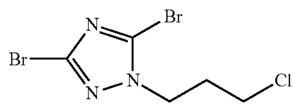 [SMILES: ClCCCn1nc(Br)nc1Br]

To a 250 mL reactor were charged 3,5-dibromo-1H-1,2,4-triazole (10 g, 44.1 mmol, Eq: 1); THF (88 g, 100 ml.); potassium carbonate (12.2 g, 88.2 mmol, Eq: 2.0) and 1-chloro-3-iodopropane (11 g, 53.8 mmol, Eq: 1.22). The mixture was stirred for 16 hours at 20° C.~25° C. Water (100 mL) was added to the reaction mixture and then extracted with EA (100 mL). The combined organic layers were washed with 20% wt NaCl aqueous solution (50 mL), dried through $Mg_2SO_4$, then concentrated to remove the solvent to afford compound (IX). The crude will used for next step without further purification.

Example 7

3,5-dibromo-1H-1,2,4-triazole (compound IX)

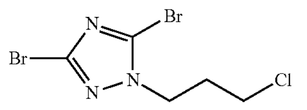 [SMILES: ClCCCn1nc(Br)nc1Br]

To a 250 mL reactor were charged 3,5-dibromo-1H-1,2,4-triazole (35 g, 154 mmol, Eq: 1); THF (88 g, 350 ml; potassium carbonate (42.6 g, 309 mmol, Eq: 2.0) and 1-chloro-3-iodopropane (31.5 g, 154 mmol, Eq: 1) at 20° C.~25° C. and stirring for 48 hours. Water (300 mL) was added to the reaction mixture and then extracted with 2-MeTHF (150 mL). The combined organic layers were washed with 20% wt NaCl aqueous solution (150 mL), dried through $Mg_2SO_4$, then concentrated to remove the solvent to afford compound (IX) (54.5 g, 78.94% purity GC-MS, 91.9% yield). The crude will used for next step without further purification.

Example 8

3,5-dibromo-1H-1,2,4-triazole (compound IX)

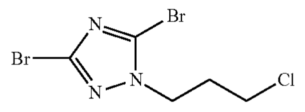 [SMILES: ClCCCn1nc(Br)nc1Br]

To a 2 L reactor were charged 3,5-dibromo-1H-1,2,4-triazole (110 g, 475 mmol, Eq: 1); THF (880 g, 1 L); potassium carbonate (134 g, 950 mmol, Eq: 2.0) and 1-chloro-3-iodopropane (129 g, 618 mmol, Eq: 1.3) at 20° C.~25° C. and stirring for 48 hours. Water (550 mL) was added to the reaction mixture and then separated, then the organic layer was washed with 20% wt NaCl aqueous solution (225 mL), dried through $Mg_2SO_4$, then concentrated to remove the solvent to afford compound (IX) (165 g, 81% purity (GC-MS), 92.7% yield). The crude will used for next step without further purification.

Example 9

2-bromo-4-(3,5-difluorophenyl)-6,7-dihydro-5H-[1,2,4]triazolo[1,5-a]pyrimidine (Compound (VIII))

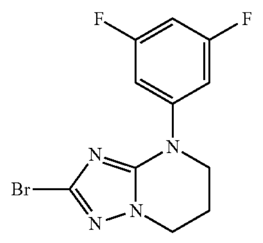 [SMILES: Fc1cc(F)cc(N2CCCn3nc(Br)nc32)c1]

To a 500 mL glass-lined reactor was charged with 3,5-difluoroaniline (5.79 g, 44.9 mmol, 1.2 eq.), compound (IX) (14 g, 37.4 mmol, 1.0 eq.) and 2-MeTHF (140 mL) at 20° C.~25° C. After being stirred for 30 min and cooled to 0~5° C., LiHMDS (1M in THF, 140 mL, 140 mmol, 3.75 eq.) was added dropwise at 0° C.~5° C. The reaction mixture was allowed warm to 20° C.~25° C. with stirring for another 1 hours. Saturated aqueous $NH_4Cl$ solution (200 mL, 10 v) was added dropwise to the reaction mixture to quench the reaction at 20~25° C. and then 20% wt NaCl aqueous solution (100 mL) was added to the reaction at 20~25° C. and stirred for 1 hours. The resulting mixture was extracted with EA (200 mL). The combined organic layer was washed with 20% wt NaCl aqueous solution (100 mL), dried through $Mg_2SO_4$, then concentrated to remove the solvent. To the resulting reaction mixture was added EA (50 mL), then heated to 50° C.~55° C., then heptane (150 mL) was added dropwise to the reaction mixture, and then cooled to 20° C.~25° C. during 6 h and stirred for another 1 h. The solid was separated via filter and washed with EA/Heptane (1/3, 10 mL), and dried in vacuum oven (30 mmHg, 40° C.) for 32 hours to afford compound (IV) (8 g, 67.2% yield, 99.0% purity) as grey solid.

Compound (VIII): 1H NMR (400 MHz, DMSO-$d_6$) δ=7.39-7.34 (m, 2H), 6.97-6.92 (m, 1H), 4.11-4.08 (m, 2H), 3.85-3.83 (m, 2H), 2.26-2.20 (m, 2H).

A series of studies were carried out to demonstrate the impact of reaction temperature and equivalent of aniline compound (IXa), which showed that 0° C.~25° C. and 1.2 eq of compound (IXa) are the best condition for this cyclization reaction:

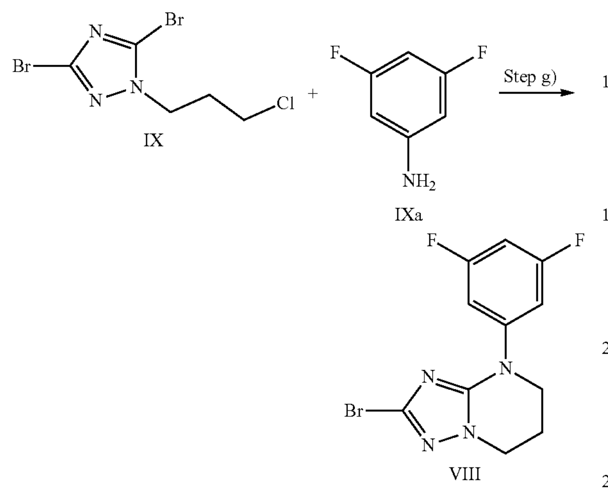

IX

IXa

VIII

| Test # | Aniline compound (IXa) | Base | Temperature | Result |
|---|---|---|---|---|
| 1 | 1.0 eq. | LIHMDS (3 eq.) | 0° C.~5° C. | 64% Conversion |
| 2 | 1.2 eq. | LiHMDS (3 eq.) | 0° C.~5° C., then 20° C.~25° C. | 81% Conversion |
| 3 | 1.5 eq. | LiHMDS (3 eq.) | 0° C.~5° C. | 100% Conversion, byproducts formed |
| 4 | 1.2 eq. | LIHMDS (2.5 eq.) | 0° C.~5° C. | 91% Conversion, byproducts formed |
| 5 | 1.2 eq. | LiHMDS (4.0 eq.) | 0° C.~5° C. | 100% Conversion, byproducts formed |
| 7 | 1.2 eq. | NaHMDS (3.0 eq.) | −20° C.~−10° C. | 69% Conversion |
| 8 | 1.2 eq. | NaHMDS (3.0 eq.) | 0° C.~5° C. | 96% Conversion, byproducts formed |
| 9 | 1.2 eq. | NaHMDS (3.0 eq.) | 20° C.~25° C. | 100% Conversion, byproducts formed |
| 10 | 1.2 eq. | NaHMDS (3.6 eq.) | 0° C.~5° C. then 20° C.~25° C. | 100% Conversion, byproducts formed |

Example 10

2-bromo-4-(3,5-difluorophenyl)-6,7-dihydro-5H-[1,2,4]triazolo[1,5-a]pyrimidine (Compound (VIII))

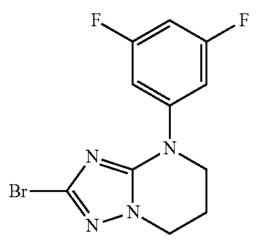 [SMILES: Fc1cc(F)cc(N2CCCn3nc(Br)nc32)c1]

To a 3 L glass-lined reactor was charged with 3,5-difluoroaniline (69.6 g, 529 mmol, 1.2 eq.), compound (IX) (165 g, 441 mmol, 1.0 eq.) and 2-MeTHF (825 mL) at 20° C.~25° C. After being stirred for 30 min and cooled to 0-5° C., LiHMDS (1.9 M in THF, 835 mL, 1.59 mol, 3.6 eq.) was added dropwise at 0° C.~5° C. The reaction mixture was allowed warm to 20° C.~25° C. with stirring for another 1 hours. Saturated aqueous $NH_4Cl$ solution (2 L, 10 v) was added dropwise to the reaction mixture to quench the reaction at 20-25° C. and then 20% wt NaCl aqueous solution (1 L) was added to the reaction at 20-25° C. and stirred for 1 hours. The resulting mixture was extracted with EA (2000 mL). The combined organic layer was washed with 20% wt NaCl aqueous solution (1 L), dried through $Mg_2SO_4$, then concentrated to remove the solvent. To the resulting reaction mixture was added EA (500 mL), then heated to 50° C.~55° C., then heptane (1.5 L) was added dropwise to the reaction mixture, and then cooled to 20° C.~25° C. during 6 h and stirred for another 1 h. The solid was separated via filter and washed with EA/Heptane (1/1, 100 mL), and dried in vacuum oven (30 mmHg, 40° C.) for 32 hours to afford compound (IV) (94 g, 67.7% yield, 98.8% purity) as grey solid.

Compound (VIII): 1H NMR (400 MHz, DMSO-$d_6$) δ=7.39-7.34 (m, 2H), 6.97-6.92 (m, 1H), 4.11-4.08 (m, 2H), 3.85-3.83 (m, 2H), 2.26-2.20 (m, 2H).

Example 11

4-(3,5-difluorophenyl)-N-[3-(6-methylpyrimidin-4-yl)-3-azabicyclo[3.2.1]octan-8-yl]-6,7-dihydro-5H-[1,2,4]triazolo[1,5-a]pyrimidin-2-amine (Compound (I))

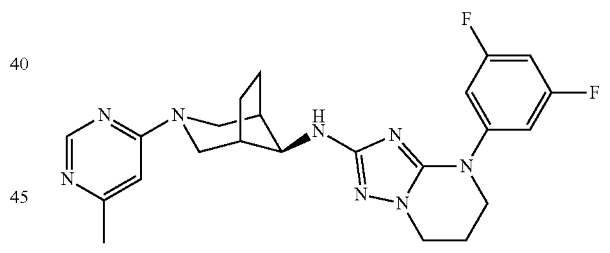

To a 50 mL One-neck flask was charged with NaOtBu (1.2 g, 12.4 mmol, Eq: 4), 2-MeTHF (10.2 g, 120 ml, 10 V), (1R,5S,8S)-3-(6-methylpyrimidin-4-yl)-3-azabicyclo[3.2.1]octan-8-amine dihydrochloride (1.06 mg, 3.42 mmol, Eq: 1.1) in one portion under $N_2$ at 20° C.~25° C. And then, to the resulting mixture were charged compound (VIII) (1 g, 3.11 mmol, Eq: 1); $Pd_2dba_3$ $CHCl_3$ (32.2 mg, 31 μmol, Eq: 0.01) and tBuXphos (26.4 mg, 62.2 μmol, Eq: 0.02) at 20° C.~25° C. The resulting mixture was heated to ~75° C. and stirred for 2 hours. The resulting mixture was cooled to 20° C.~25° C., water (10 mL) and MeOH (10 mL) was added, and then extracted with 2-MeTHF (25 mL) twice. The combined organic layer was filter through MCC pad, then concentrated to remove solvents. To the residual was added 2-MeTHF (5 mL), and then the reaction mixture was heated to 20° C.~25° C. Heptane (15 mL) was added dropwise to the reaction mixture, then cooled to 20° C.~25° C. and stirred for another hours. The product was collected via filter and washed with heptane (2 ml), and dried in vacuum oven (30 mmHg, 40° C.) for 16 hours to afford compound (IV) (1.1 g, 77.5% yield, 98.8% purity).

Compound (VI): 1H NMR (400 MHz, DMSO-$d_6$) δ ppm 8.35 (s, 1H), 7.45 (dd, J=10.6, 2.0 Hz, 2H), 6.78-6.86 (m, 1H), 6.63 (s, 1H), 5.84 (d, J=4.1 Hz, 1H), 3.96-4.41 (m, 2H), 3.93 (t, J=6.0 Hz, 2H), 3.75-3.81 (m, 2H), 3.54 (d, J=4.1 Hz, 1H), 2.96 (br d, J=12.1 Hz, 2H), 2.44 (br s, 2H), 2.25 (s, 3H), 2.19 (quin, J=5.8 Hz, 2H), 1.83-1.88 (m, 2H), 1.27-1.33 (m, 2H).

$^{13}$C NMR (101 MHz, DMSO-$d_6$) δ ppm 21.85 (s, 1C), 24.20 (s, 1C), 25.74 (s, 2C), 38.73 (s, 2C), 43.86 (s, 1C), 45.64 (s, 1C), 50.63 (s, 2C), 62.08 (s, 1C), 97.20 (t, J=26.41 Hz, 1C), 101.92 (s, 1C), 102.81 (d, J=29.34 Hz, 2C), 145.80 (t, J=13.94 Hz, 1C), 149.51 (s, 1C), 157.61 (s, 1C), 160.39 (s, 1C), 162.79 (dd, J=242.09, 16.14 Hz, 2C), 163.20 (s, 1C), 164.75 (s, 1C)

$^{19}$F NMR (376 MHz, DMSO-$d_6$) δ=−110.00-1110.13 (m, 2F) [α]$D^{25}$=0.199°

HRMS: calculated 453.225 $[C_{23}H_{26}F_2N_8+H]^+$. found 453.2354 $[M+H]^+$

Example 12

4-(3,5-difluorophenyl)-N-[3-(6-methylpyrimidin-4-yl)-3-azabicyclo[3. 2. 1]octan-8-yl]-6, 7-dihydro-5H-[1, 2, 4]triazolo[1,5-a]pyrimidin-2-amine (Compound (I))

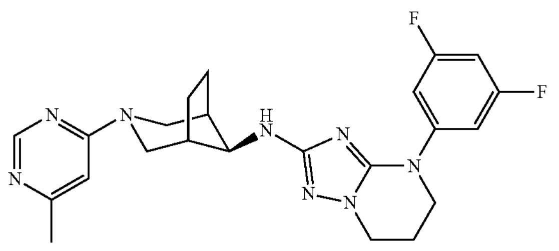

To a 250 mL One-neck flask was charged with NaOtBu (12 g, 124 mmol, Eq: 4), 2-MeTHF (102 g, 120 ml, 10 V), (1R,5S,8S)-3-(6-methylpyrimidin-4-yl)-3-azabicyclo[3.2.1] octan-8-amine dihydrochloride (10.7 g, 34.2 mmol, Eq: 1.1) in one portion under $N_2$ at 20° C.~25° C. And then, to the resulting mixture were charged compound (VIII) (10 g, 31.1 mmol, Eq: 1); $Pd_2dba_3\cdot CHCl_3$ (322 mg, 311 μmol, Eq: 0.01) and tBuXphos (264 mg, 622 μmol, Eq: 0.02) at 20° C.~25° C. The resulting mixture was heated to 75° C. and stirred for 2 hours. The resulting mixture was cooled to 20° C.~25° C., water (100 mL) and MeOH (100 mL) was added, and then extracted with 2-MeTHF (250 mL) twice. The combined organic layer was filter through MCC (Microcrystalline Cellulose) pad, then concentrated to remove solvents. To the residual was added 2-MeTHF (50 mL), and then the reaction mixture was heated to 20° C.~25° C. Heptane (150 mL) was added dropwise to the reaction mixture, then cooled to 20° C.~25° C. and stirred for another 10 hours. The product was collected via filter and washed with heptane (20), and dried in vacuum oven (30 mmHg, 40° C.) for 16 hours to afford compound (I) (12 g, 85% yield, 98.1% purity).

Compound (I): 1H NMR (400 MHz, DMSO-$d_6$) δ ppm 8.35 (s, 1H), 7.45 (dd, J=10.6, 2.0 Hz, 2H), 6.78-6.86 (m, 1H), 6.63 (s, 1H), 5.84 (d, J=4.1 Hz, 1H), 3.96-4.41 (m, 2H), 3.93 (t, J=6.0 Hz, 2H), 3.75-3.81 (m, 2H), 3.54 (d, J=4.1 Hz, 1H), 2.96 (br d, J=12.1 Hz, 2H), 2.44 (br s, 2H), 2.25 (s, 3H), 2.19 (quin, J=5.8 Hz, 2H), 1.83-1.88 (m, 2H), 1.27-1.33 (m, 2H).

$^{13}$C NMR (101 MHz, DMSO-$d_6$) δ ppm 21.85 (s, 1C), 24.20 (s, 1C), 25.74 (s, 2C), 38.73 (s, 2C), 43.86 (s, 1C), 45.64 (s, 1C), 50.63 (s, 2C), 62.08 (s, 1C), 97.20 (t, J=26.41 Hz, 1C), 101.92 (s, 1C), 102.81 (d, J=29.34 Hz, 2C), 145.80 (t, J=13.94 Hz, 1C), 149.51 (s, 1C), 157.61 (s, 1C), 160.39 (s, 1C), 162.79 (dd, J=242.09, 16.14 Hz, 2C), 163.20 (s, 1C), 164.75 (s, 1C)

$^{19}$F NMR (376 MHz, DMSO-$d_6$) δ=−110.00-1110.13 (m, 2F) [α]$D^{25}$=0.199°

HRMS: calculated 453.225 $[C_{23}H_{26}F_2N_8+H]^+$. found 453.2354 $[M+H]^+$

Example 13

4-(3,5-difluorophenyl)-N-[3-(6-methylpyrimidin-4-yl)-3-azabicyclo[3.2.1]octan-8-yl]-6,7-dihydro-5H-[1,2,4]triazolo[1,5-a]pyrimidin-2-amine (Compound (I))

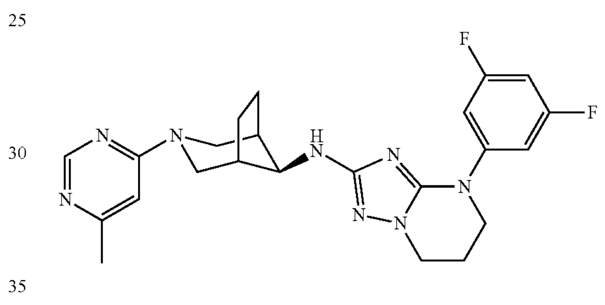

To a 5 L 3-neck flask was charged with NaOtBu (191 g, 1.99 mol, Eq: 4), 2-MeTHF (1.6 L, 10 V), (1R,5S,8S)-3-(6-methylpyrimidin-4-yl)-3-azabicyclo[3.2.1]octan-8-amine dihydrochloride (171 g, 547 mmol, Eq: 1.1) in one portion under $N_2$ at 20° C.~25° C. And then, to the resulting mixture were charged compound (VIII) (160 g, 498 mmol, Eq: 1); $Pd_2$ $(dba_3)\cdot CHCl_3$ (4.56 g, 4.98 mmol, Eq: 0.01) and tBuXphos (4.23 g, 9.95 mmol, Eq: 0.02) at 20° C.~25° C. The resulting mixture was heated to 70° C.~75° C. and stirred for 2 hours. To the resulting mixture was added heptane (1.6 L) and then cooled to 20° C.~25° C. The crude solid was collected via filter and rinsed with Hep/2-MeTHF (1:1, 150 mL). The resulting cake was slurried with water and stirred for 2 hours at 20° C.~25° C. The crude solid was collected via filter and rinsed with water (200 mL). The resulting cake was diluted with MeOH (400 mL) and DCM (1 L) in a 2 L reactor. Charcoal (20 g) was added to the suspension and was heated to 60° C.~65° C. with stirring for 2 hours, then cooled to 20° C.~25° C. The suspension was filtered through celite, rinsed with MeOH/DCM (4:10, 100 mL). The filtrate was concentrated and the residual was diluted with 2-MeTHF (500 mL), heated to 60° C.~65° C. and stirred for 30 min. Heptane (1500 mL) was added dropwise to the resulting mixture at 60° C.~65° C., then allowed cooled to 60° C.~65° C. and stirred for 10 hours. The crude was collected via filter and rinsed with heptane (200 mL), then the cake was diluted with water (160 ml) and adjust pH to 3-4 with HCl (36.5% wt., 129 mL). To the resulting reaction mixture was added NaOH (1M, 568 mL), adjust pH back to 7-8, the resulting mixture was stirred at 1 hours at 20° C.~25° C. The product was collected via filter and washed with heptane (20), and dried in vacuum oven (30 mmHg, 40° C.) for 16 hours to afford compound (I) (200 g, 87.9% yield, 98.98% purity).

Compound (I): $^{1}H$ NMR (400 MHz, DMSO-$d_6$) δ ppm 8.35 (s, 1H), 7.45 (dd, J=10.6, 2.0 Hz, 2H), 6.78-6.86 (m, 1H), 6.63 (s, 1H), 5.84 (d, J=4.1 Hz, 1H), 3.96-4.41 (m, 2H), 3.93 (t, J=6.0 Hz, 2H), 3.75-3.81 (m, 2H), 3.54 (d, J=4.1 Hz, 1H), 2.96 (br d, J=12.1 Hz, 2H), 2.44 (br s, 2H), 2.25 (s, 3H), 2.19 (quin, J=5.8 Hz, 2H), 1.83-1.88 (m, 2H), 1.27-1.33 (m, 2H).

$^{13}C$ NMR (101 MHz, DMSO-$d_6$) δ ppm 21.85 (s, 1C), 24.20 (s, 1C), 25.74 (s, 2C), 38.73 (s, 2C), 43.86 (s, 1C), 45.64 (s, 1C), 50.63 (s, 2C), 62.08 (s, 1C), 97.20 (t, J=26.41 Hz, 1C), 101.92 (s, 1C), 102.81 (d, J=29.34 Hz, 2C), 145.80 (t, J=13.94 Hz, 1C), 149.51 (s, 1C), 157.61 (s, 1C), 160.39 (s, 1C), 162.79 (dd, J=242.09, 16.14 Hz, 2C), 163.20 (s, 1C), 164.75 (s, 1C)

$^{19}F$ NMR (376 MHz, DMSO-$d_6$) δ=−110.00-1110.13 (m, 2F) [α]$D^{25}$=0.199°

HRMS: calculated 453.225 $[C_{23}H_{26}F_2N_8+H]^+$. found 453.2354 $[M+H]^+$

The invention claimed is:

1. A process for the preparation of a compound of formula (VIII):

(VIII)

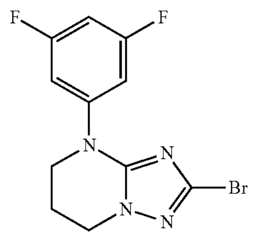

wherein the process comprises the following steps:

(a) reacting a compound of formula (II):

(II)

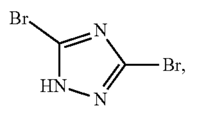

with a compound of the following formula:

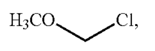

to provide a compound of formula (III):

(III)

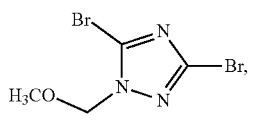

(b) reacting the compound of formula (III) above with a compound of the following formula:

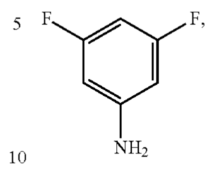

to provide a compound of formula (IV):

(IV)

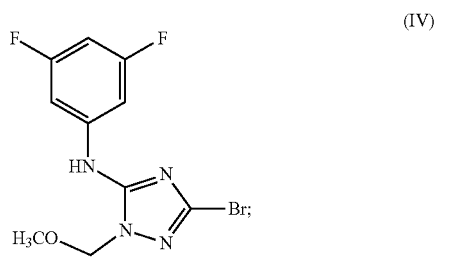 [SMILES: COCn1nc(Br)nc1Nc1cc(F)cc(F)c1]

(c) reacting the compound of formula (IV) above with a compound of formula (V):

(V)

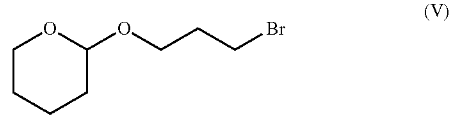 [SMILES: BrCCCOC1CCCCO1]

to provide a compound of formula (VI):

(VI)

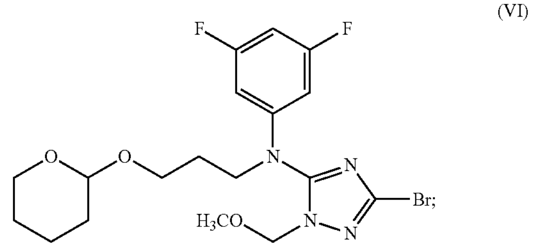 [SMILES: COCn1nc(Br)nc1N(CCCOC1CCCCO1)c1cc(F)cc(F)c1]

(d) reacting the compound of formula (VI) above with an acid selected from the group consisting of hydrobromic acid (HBr), hydrochloric acid (HCl), and trifluoroacetic acid (TFA), to provide a compound of formula (VII):

(VII)

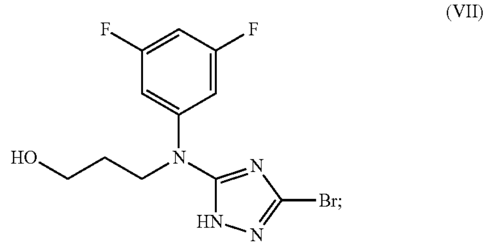 [SMILES: OCCCN(c1cc(F)cc(F)c1)c1nc(Br)n[nH]1]

and (e) reacting the compound of formula (VII) above under Mitsunobu conditions using triphenylphosphine in the presence of diethyl azodicarboxylate (DEAD) and a solvent selected from the group consisting of dimethylformamide (DMF), dimethyl sulfoxide (DMSO), and N-methyl-2-pyrrolidone (NMP), to provide a compound of formula (VIII):

(VIII)

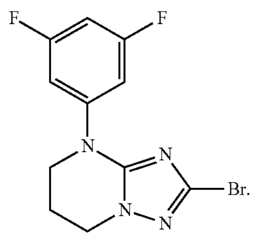

2. The process according to claim 1, wherein in step (a), the reaction is performed in the presence of a base selected from the group consisting of sodium hydride (NaH), sodium acetate (NaOAc), and potassium acetate (KOAc).

3. The process according to claim 1, wherein in step (a), the reaction is performed in the presence of a solvent selected from the group consisting of dichloromethane (DCM) and tetrahydrofuran (THF).

4. The process according to claim 1, wherein in step (b), the amount of 3,5-difluoroaniline is in the range of from 1.0 equivalent to 2.5 equivalents.

5. The process according to claim 1, wherein in step (b), the reaction is performed in the presence of a base selected from the group consisting of lithium bis(trimethylsilyl) amide (LiHMDS), sodium bis(trimethylsilyl)amide (NaHMDS), sodium hydride (NaH), sodium hydroxide (NaOH), potassium carbonate ($K_2CO_3$), and potassium hydroxide (KOH).

6. The process according to claim 5, wherein the amount of the base is in the range of from 1.0 equivalent to 2.5 equivalents.

7. The process according to claim 1, wherein in step (b), the reaction is performed in the presence of a solvent selected from the group consisting of dichloromethane (DCM), tetrahydrofuran (THF), and 2-methyltetrahydrofuran (2-MeTHF).

8. The process according to claim 1, wherein in step (b), the reaction is performed at a temperature in the range of −20° C. to 70° C.

9. The process according to claim 1, wherein in step (c), the amount of the compound of formula (V) is in the range of from 1.7 equivalents to 2.26 equivalents.

10. The process according to claim 1, wherein in step (c), the reaction is performed in the presence of a base selected from the group consisting of cesium carbonate ($Cs_2CO_3$), sodium carbonate ($Na_2CO_3$), potassium carbonate ($K_2CO_3$), and sodium hydroxide (NaOH).

11. The process according to claim 10, wherein the amount of the base is in the range of from 2.0 equivalents to 3.0 equivalents.

12. The process according to claim 1, wherein in step (d), the reaction is performed in the presence of hydrochloric acid (HCl).

13. The process according to claim 12, wherein the volume of hydrochloric acid (HCl) is in the range of from 1.0 V to 2.0 V.

14. The process according to claim 1, wherein in step (e), the reaction is performed in the presence of dimethylformamide (DMF).

15. The process according to claim 14, wherein the volume of dimethylformamide (DMF) is in the range of from 5.0 V to 10.0 V.

* * * * *